US010692188B2

(12) United States Patent
Zeraatkar et al.

(10) Patent No.: US 10,692,188 B2
(45) Date of Patent: Jun. 23, 2020

(54) PEAK DETECTION IN A TWO DIMENSIONAL IMAGE

(71) Applicants: Navid Zeraatkar, Tehran (IR); Salar Sajedi Toighoun, Tehran (IR); Mohsen Taheri Parkoohi, Tehran (IR); Mohammad Reza Ay, Tehran (IR); Mohammad Hossein Farahani, Tehran (IR); Saeed Sarkar, Tehran (IR)

(72) Inventors: Navid Zeraatkar, Tehran (IR); Salar Sajedi Toighoun, Tehran (IR); Mohsen Taheri Parkoohi, Tehran (IR); Mohammad Reza Ay, Tehran (IR); Mohammad Hossein Farahani, Tehran (IR); Saeed Sarkar, Tehran (IR)

(73) Assignee: TOSE'E SANAYE TASVIRBARDARI PARTO NEGAR PERSIA COMPANY LTD., Tehran (IR)

( * ) Notice: Subject to any disclaimer, the term of this patent is extended or adjusted under 35 U.S.C. 154(b) by 276 days.

(21) Appl. No.: 15/829,808

(22) Filed: Dec. 1, 2017

(65) Prior Publication Data
US 2018/0101936 A1  Apr. 12, 2018

Related U.S. Application Data

(60) Provisional application No. 62/429,763, filed on Dec. 3, 2016.

(51) Int. Cl.
*G06K 9/00* (2006.01)
*G06T 5/00* (2006.01)
(Continued)

(52) U.S. Cl.
CPC .............. *G06T 5/002* (2013.01); *A61B 6/037* (2013.01); *A61B 6/582* (2013.01);
(Continued)

(58) Field of Classification Search
USPC ......................................... 382/131
See application file for complete search history.

(56) References Cited

U.S. PATENT DOCUMENTS 6,721,461 B1 * 4/2004 Nichani ................. G06K 9/38
                                                     382/145
7,026,621 B2    4/2006 Stonger
(Continued)

FOREIGN PATENT DOCUMENTS

CN        102981179       12/2014
JP          5024566        9/2012

OTHER PUBLICATIONS

Hung et al. "Development of correction schemes for a small field of view gamma camera." Biomedical Engineering Letters, 2012, vol. 2, No. 4, pp. 215-222.
(Continued)

*Primary Examiner* — Stephen P Coleman
(74) *Attorney, Agent, or Firm* — Bajwa IP Law Firm; Haris Zaheer Bajwa

(57) ABSTRACT

An improved method for peak detection in a two-dimensional image is disclosed. In one implementation, the method includes one or more of the following steps: generating a smooth image from the two-dimensional image, detecting a plurality of local peaks in the smooth image, detecting a plurality of true peaks among the plurality of local peaks, and generating a peak-detected image from the smooth image. The smooth image includes a plurality of pixels, where each pixel of the plurality of pixels has an intensity level and an address. The address includes a row number and a column number. The peak-detected image includes a first true peaks subset from the plurality of true peaks. In one implementation, the intensity level of each true peak of the first true peaks subset is higher than an intensity (Continued)

threshold. The method further includes localizing at least one true peak of the first true peaks subset in the peak-detected image.

19 Claims, 7 Drawing Sheets

(51) Int. Cl.
| | |
|---|---|
| G06T 5/20 | (2006.01) |
| G06T 11/00 | (2006.01) |
| A61B 6/03 | (2006.01) |
| C09K 11/77 | (2006.01) |
| A61B 6/00 | (2006.01) |
| G01T 1/00 | (2006.01) |
| G01T 7/00 | (2006.01) |
| G06T 7/13 | (2017.01) |
| G01T 1/29 | (2006.01) |

(52) U.S. Cl.
CPC ............ *C09K 11/7774* (2013.01); *G01T 1/00* (2013.01); *G01T 1/2985* (2013.01); *G01T 7/005* (2013.01); *G06T 5/20* (2013.01); *G06T 7/13* (2017.01); *G06T 11/005* (2013.01); *G06T 2207/10104* (2013.01); *G06T 2207/10108* (2013.01); *G06T 2210/41* (2013.01)

(56) References Cited

U.S. PATENT DOCUMENTS

| | | | |
|---|---|---|---|
| 7,232,990 B2 | 6/2007 | Wang | |
| 8,117,142 B2 | 2/2012 | Hu | |
| 8,471,211 B2 | 6/2013 | Yamada | |
| 8,750,569 B2 | 6/2014 | Laurence | |
| 2010/0283785 A1* | 11/2010 | Satulovsky | G01N 27/447 345/440 |
| 2012/0249297 A1* | 10/2012 | Du | G07C 9/00158 340/5.82 |
| 2012/0283564 A1* | 11/2012 | Ebbini | A61B 8/06 600/439 |

OTHER PUBLICATIONS

Lazzerini et al. "Calibration of positron emission tomograph detector modules using new neural method." Electronics Letters, 2004, vol. 40, No. 6, pp. 360-361.

Bruyndonckx et al. "Neural network-based position estimators for PET detectors using monolithic LSO blocks." IEEE Transactions on Nuclear Science, 2004, vol. 51, No. 5, pp. 2520-2525.

Hu et al. "A neural network based algorithm for building crystal look-up table of PET block detector." In Nuclear Science Symposium Conference Record, 2006. IEEE, Oct. 2006, vol. 4, pp. 2458-2461.

Chaudhari et al. "Crystal identification in positron emission tomography using nonrigid registration to a Fourier-based template." Physics in medicine and biology, 2008, vol. 53, No. 18, p. 5011.

Chaudhari et al. "Spatial distortion correction and crystal identification for MRI-compatible position-sensitive avalanche photodiode-based PET scanners." IEEE transactions on nuclear science, 2009, vol. 56, No. 3, pp. 549-556.

Schellenberg et al. "An algorithm for automatic crystal identification in pixelated scintillation detectors using thin plate splines and Gaussian mixture models." Physics in medicine and biology, 2016, vol. 61, No. 3, pp. N90-N101.

Yoshida et al. "Calibration procedure for a DOI detector of high resolution PET through a Gaussian mixture model." IEEE Transactions on Nuclear Science, 2004, vol. 51, No. 5, pp. 2543-2549.

Maisler et al. "Voronoi Diagram and its Application to Spatial Calibration for Gamma Camera Images." In GRAPP, 2008, pp. 68-73.

Tao, "Development of a silicon photomultiplier based gamma camera." PhD diss., 2012.

González et al. "A PET design based on SiPM and monolithic LYSO crystals: performance evaluation." IEEE Transactions on Nuclear Science, 2016, vol. 63, No. 5, pp. 2471-2477.

Brown et al. "influence of depth of interaction upon the performance of scintillator detectors." PloS one, 2014, vol. 9, No. 5, p. e98177.

Thompson et al. "Measurement of energy and timing resolution of very highly pixellated LYSO crystal blocks with multiplexed SiPM readout for use in a small animal PET/MR insert." In Nuclear Science Symposium and Medical Imaging Conference (NSS/MIC), 2013. IEEE, Oct. 2013, pp. 1-5.

Aguiar et al. "A feasibility study on the use of arrays of discrete SiPMs for MR compatible LYSO readout using Monte Carlo simulation." Journal of Instrumentation, 2012, vol. 7, No. 06, p. P06002.

Jeong et al. Position mapping, energy calibration, and flood correction improve the performances of small gamma camera using PSPMT. In Nuclear Science Symposium Conference Record, 2003. IEEE, Oct. 2003, vol. 3, pp. 2103-2107.

Pichler et al. "Detector characterization and detector setup of a NaI-LSO PET/SPECT camera." IEEE Transactions on Nuclear Science, 2003, vol. 50, No. 5, pp. 1420-1427.

\* cited by examiner

PEAK DETECTION IN A TWO DIMENSIONAL IMAGE

CROSS-REFERENCE TO RELATED APPLICATION

This application claims the benefit of priority from U.S. Provisional Patent Application Ser. No. 62/429,763, filed on Dec. 3, 2016, and entitled "AUTOMATIC 2D PEAK DETECTION FOR CALIBRATION OF GAMMA DETECTOR BLOCK IMAGES," which is incorporated herein by reference in its entirety.

SPONSORSHIP STATEMENT

This application has been sponsored by Iran Patent Office, which does not have any rights in this application.

TECHNICAL FIELD

The present disclosure relates generally to image processing, and particularly, to peak detection in two dimensional images.

BACKGROUND

Peak detection is a necessary process in many two-dimensional images, for example, in nuclear medicine imaging systems, such as single-photon emission computed tomography (SPECT) and positron emission tomography (PET). These systems include gamma detectors, in which pixelated scintillation crystals may be applied. Such pixelated crystals may be optically coupled with an array of photocathodes. Interaction of gamma photons with a scintillator produces light photons. The light photons are then converted to electrons by interacting with the photocathode after they pass through the scintillator crystal. Subsequently, the electrons are converted to electric signals and amplified in front-end electronics in order to be translated to information relating to incidence position of a primary gamma photon to the crystal. Due to noise and errors in detection systems, there is an uncertainty in estimating the incidence position of the gamma photons. Given such uncertainty in positioning, a positioning calibration may be necessary in nuclear medicine imaging modalities. When pixelated crystals are used, a two-dimensional image which includes some hot points (also referred to as peaks), each corresponding to a pixel, is generated by irradiating the crystal with a uniform emission of gamma photons. Such a two-dimensional image may be referred to as a "flood image." Since the flood-field image may have a low quality and the response of each pixel may be a blurry point in a noisy background, determining the peak position of each blurry response may be needed.

The process of locating the position of these peaks is sometimes referred to as peak detection, and is one of the primary steps in a position calibration procedure. Performance of peak detection has a significant impact on positioning and imaging quality. Various algorithms have been developed for peak detection. However, these algorithms fail to provide appropriate results when noisy images are generated in nuclear medicine imaging. Manual methods are also used in which a user determines the peak position. However, such methods are highly dependent on the user's skill. In addition, they suffer from not being reproducible, high inter-variability, and time consumption when there are many detector blocks to be calibrated.

There is therefore a need for an automatic peak detection algorithm that can provide accurate results in the presence of noise and distortion. There is also a need for a method that accurately maps each detected peak in the peak-detected image to the true position of the corresponding pixel in the original two-dimensional image.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes a method for peak detection in a two-dimensional image. The method may include one or more of the following steps: generating a smooth image from the two-dimensional image, detecting a plurality of local peaks in the smooth image, detecting a plurality of true peaks among the plurality of local peaks, and generating a peak-detected image from the smooth image. The smooth image may include a plurality of pixels. Each pixel of the plurality of pixels may include an intensity level and an address. The address may include a row number and a column number. In some implementations, the peak-detected image may include a first true peaks subset from the plurality of true peaks. In addition, the intensity level of each true peak of the first true peaks subset may be higher than an intensity threshold. The method may include localizing at least one true peak of the first true peaks subset in the peak-detected image.

The above general aspect may include one or more of the following features. In some implementations, generating the smooth image may include applying a smoothing function on the two-dimensional image. Furthermore, the smoothing function may include a normalized two-dimensional Gaussian filter.

In some implementations, detecting the plurality of local peaks may include placing a two-dimensional window on a portion of the smooth image, selecting a first pixels subset from the plurality of pixels, and detecting a local peak of the plurality of local peaks. The first pixels subset may be located inside the two-dimensional window, and the local peak may coincide with a first pixel in the first pixels subset. In some examples, the first pixel may have the highest intensity level in the first pixels subset.

In some implementations, detecting the plurality of true peaks may include defining a neighborhood around a second pixel of the plurality of pixels, selecting a local peaks subset from the plurality of local peaks, and detecting a first true peak of the plurality of true peaks. The local peaks subset may be located in the neighborhood. In some cases, the first true peak may coincide with the second pixel, if size of the local peaks subset is larger than a peak size threshold. In some implementations, the neighborhood may include a second pixels subset from the plurality of pixels. The absolute difference of the row number of each pixel of the second pixels subset and the row number of the second pixel may be smaller than two, and the absolute difference of the column number of each pixel of the second pixels subset and the column number of the second pixel may be smaller than two.

In some examples, generating the peak-detected image may include selecting a third pixel from the plurality of pixels, selecting a second true peak from the plurality of true peaks, and setting the intensity levels of the third pixel and the second true peak to zero. The third pixel may not be included in the plurality of true peaks, and the intensity level of the second true peak may be smaller than the intensity threshold.

In some implementations, the method may further include detecting an updated plurality of local peaks in the peak-detected image, detecting an updated plurality of true peaks among the updated plurality of local peaks, replacing the plurality of true peaks with the updated plurality of true peaks, generating an updated peak-detected image from the peak-detected image, and replacing the peak-detected image with the updated peak-detected image. The updated peak-detected image may include an updated true peaks subset from the plurality of true peaks.

In some implementations, localizing at least one true peak of the first true peaks subset may include defining a square region around a third true peak from the first true peaks subset, where the third true peak may be located at the center of the square region, calculating a center of mass of the square region, and relocating the third true peak to the center of mass of the square region.

In some implementations, the method may further include defining a plurality of bands in the peak-detected image. Each band of the plurality of bands may include a plurality of rows of the peak-detected image. The plurality of rows may include a second true peaks subset from the plurality of true peaks. The number of true peaks in the second true peaks subset may be equal to a given peak number, or larger than the given peak number. In some examples, defining the plurality of bands may include selecting a first row from the plurality of rows, selecting a second row from the plurality of rows where the second row may be equal to the first row, selecting the second true peaks subset from the plurality of true peaks, comparing the number of true peaks in the second true peaks subset with the given peak number, replacing the second row with a third row of the plurality of rows if the number of true peaks in the second true peaks subset is smaller than the given peak number, and defining a band of the plurality of bands as a rows subset in the peak-detected image, if the number of true peaks in the second true peaks subset is equal to or larger than the given peak number. Each true peak in the second true peaks subset may be located in the first row, or in the second row, or in a portion of the peak-detected image between the first row and the second row. In addition, the rows subset may include the first row, the second row and a portion of the peak-detected image between the first row and the second row. The third row may be located below the second row. In some cases, selecting the second true peaks subset, comparing the number of true peaks in the second true peaks subset with the given peak number, and replacing the second row with the third row may be repeated in a cycle until the number of true peaks in the second true peaks subset becomes equal to or larger than the given peak number. In some cases, defining the plurality of bands may further include replacing the first row with a fourth row in the peak-detected image after the band in the plurality of bands is defined, if the second row is not a last row in the peak-detected image. The fourth row may be located below the second row.

In some implementations, the two-dimensional image may include a digitized flood-field image generated in a gamma detector of a nuclear medicine imaging system. In some examples, the gamma detector may include a plurality of pixelated scintillation crystals optically coupled with an array of photo-detectors. In addition, the nuclear medicine imaging system may include a positron emission tomography (PET) imaging system, or a single-photon emission computed tomography (SPECT) imaging system. The digitized flood-field image may be used in a calibration process including a positioning calibration in the positron emission tomography imaging system, or a linearity calibration in the single-photon emission computed tomography imaging system. In some implementations, the positioning calibration and the linearity calibration may include irradiating the plurality of pixelated scintillation crystals by a uniform radiation source. In other implementations, the positioning calibration and the linearity calibration may include radiation from the plurality of pixelated scintillation crystals. The plurality of pixelated scintillation crystals may include a plurality of Lutetium based crystals.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

The following detailed description is presented to enable a person skilled in the art to make and use the methods and devices disclosed in exemplary implementations of the present disclosure. For purposes of explanation, specific nomenclature is set forth to provide a thorough understanding of the present disclosure. However, it will be apparent to one skilled in the art that these specific details are not required to practice the disclosed exemplary implementations. Descriptions of specific exemplary implementations are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Disclosed herein is a method for peak detection in a two-dimensional image. The method may include generating a smooth image from the two-dimensional image, and generating a peak-detected image from the smooth image. Generating the peak-detected image may include detecting a plurality of local peaks in the smooth image, and detecting a plurality of true peaks among the plurality of local peaks. The method may further include localizing each of the plurality of true peaks in the peak detected image, and defining a plurality of bands. Each band may include a given number of true peaks in the peak-detected image.

Figure 1:
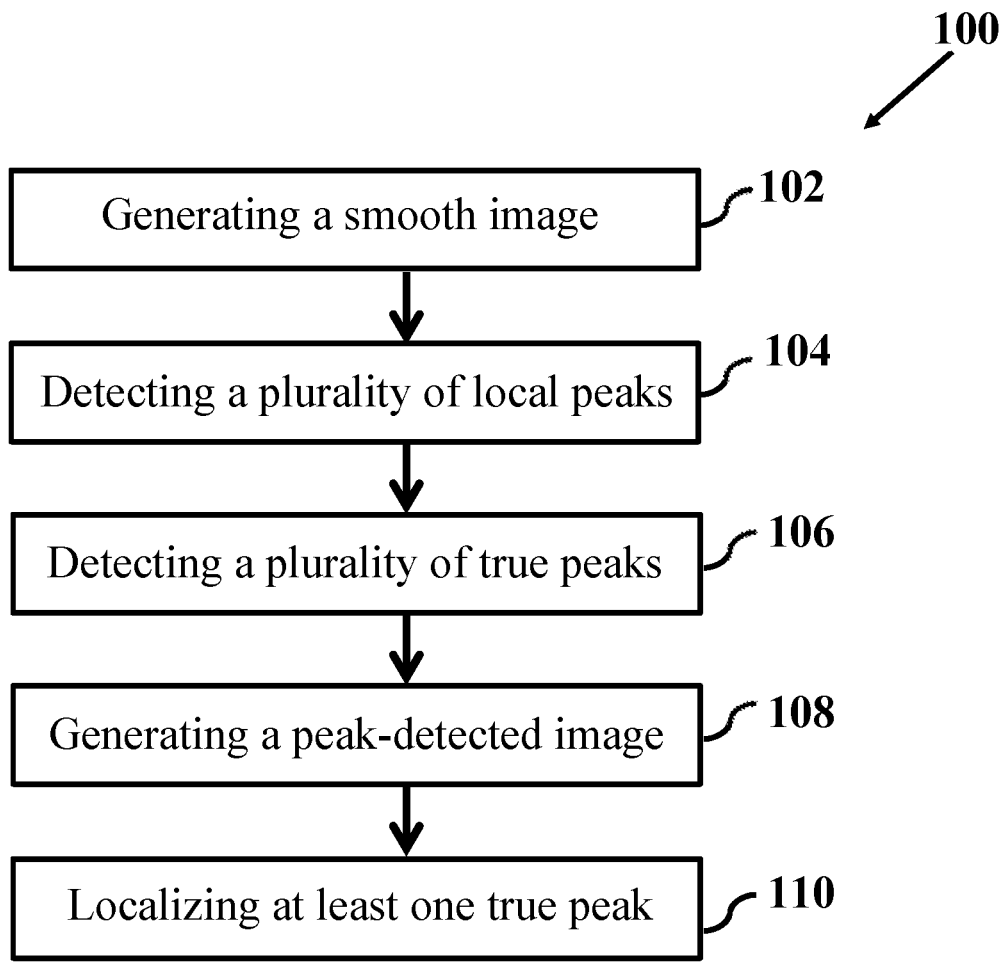
FIG. 1 is a flowchart illustrating an implementation of a method for peak detection in a two-dimensional image.

FIG. 1 illustrates a flowchart for an implementation of a method 100 for peak detection in a two-dimensional image. The method 100 may include one or more of the following steps: generating a smooth image from the two-dimensional image (step 102), detecting a plurality of local peaks in the smooth image (step 104), detecting a plurality of true peaks among the plurality of local peaks (step 106), generating a peak-detected image from the smooth image (step 108), where the peak-detected image may include a first true peaks subset from the plurality of true peaks, and localizing at least one true peak of the first true peaks subset in the peak-detected image (step 110). In some implementations, the intensity level of each true peak of the first true peaks subset may be higher than an intensity threshold. Each of these steps will be described in more detail below.

In some implementations, the two-dimensional image may include a digitized flood-field image that is generated in a gamma detector of a nuclear medicine imaging system. In some systems, gamma detectors used to generate such flood-field images include a plurality of pixelated scintillation crystals that are optically coupled with an array of photodetectors. In addition, some nuclear medicine imaging systems include a positron emission tomography (PET) imaging system, or a single-photon emission computed tomography (SPECT) imaging system.

The digitized flood-field image may be used in a calibration process. In some implementations, the calibration process may include a positioning calibration in the positron emission tomography imaging system. In other implementations, the calibration process may include a linearity calibration in the single-photon emission computed tomography imaging system. In an implementation, the positioning calibration and the linearity calibration may include irradiating the plurality of pixelated scintillation crystals by a uniform radiation source. In another implementation, the positioning calibration and the linearity calibration may include radiation from the plurality of pixelated scintillation crystals. In an example, the plurality of pixelated scintillation crystals may include a plurality of Lutetium based crystals.

Figure 2:
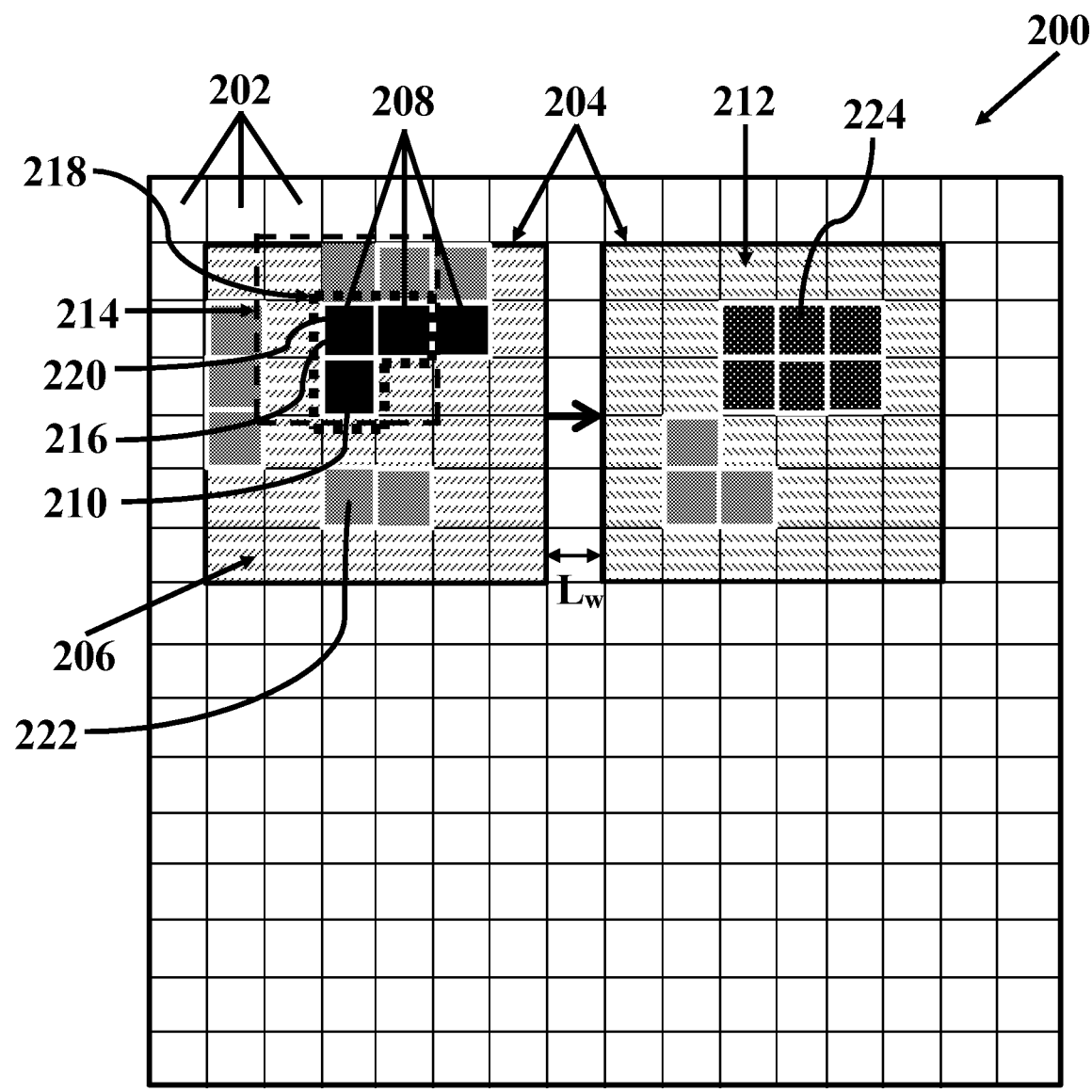
FIG. 2 illustrates an implementation of a smooth image generated from a two-dimensional image, including a plurality of pixels, local peaks, and true peaks.

FIG. 2 illustrates example pixels in a smooth image 200. As shown, the smooth image 200 may include a plurality of pixels 202 (though only three pixels are pointed to in the drawings, the plurality of pixels 202 refer to all the pixels in the smooth image 200). Each of the plurality of pixels 202 may have an intensity level and an address. The address may include a row number and a column number.

In some implementations, generating the smooth image (step 102) may include applying a smoothing function on the two-dimensional image. In an example, the smoothing function may include a normalized two-dimensional Gaussian filter. Normalization of the Gaussian filter may prevent the pixel intensity levels in the smooth image from exceeding the maximum available dynamic range for image processing. The Gaussian filter may include a kernel size and a standard deviation. The kernel size may be set according to the standard deviation to include a sufficiently large portion of the Gaussian filter, in terms of the standard deviation. However, a larger kernel size increases computational burden. The process of generating the smooth image (step 102) can be formulated as $$I_F = I * F \quad (1)$$

where I is the two-dimensional image, F is the smoothing function, $I_F$ is the smooth image 200 and '*' is the convolution operator.

In some implementations, detecting the plurality of local peaks (step 104) may include placing a two-dimensional window 204 on a portion of the smooth image 200, selecting a first pixels subset 206 (represented by hatched squares in FIG. 2) from those plurality of pixels 202 that fall within the two-dimensional window 204, and detecting a local peak (of the plurality of local peaks 208, represented by three examples in FIG. 2). The local peak may coincide with a first pixel 210 in the first pixels subset 206. In some implementations, the first pixel 210 (represented in black in FIG. 2), may have a highest intensity level. In some implementations, the two-dimensional window 204 may be moved on the smooth image 200 to a new position according to a window step $L_w$, after detecting the local peak, to detect a new member of the plurality of local peaks 208 in a new portion 212 of the smooth image 200.

In some implementations, detecting the plurality of true peaks (step 106) may include defining a neighborhood 214 around a second pixel 216 of the plurality of pixels 202, selecting a local peaks subset 218 from the plurality of local peaks 208, and detecting a first true peak 220 of the plurality of true peaks. The first true peak 220 may coincide with the second pixel 216, if size of the local peaks subset 218 is larger than a peak size threshold. In addition, the local peaks subset 218 may be located in the neighborhood 214. In some implementations, the neighborhood 214 may be moved to a new position around a new pixel of the plurality of pixels 202 after detecting the first true peak 220, to detect a new true peak of the plurality of true peaks.

In some implementations, the neighborhood 214 may include a second pixels subset from the plurality of pixels 202. In one implementation, the absolute difference of the row number of each pixel of the second pixels subset and the row number of the second pixel 216 is smaller than two, and the absolute difference of the column number of each pixel of the second pixels subset and the column number of the second pixel 216 should be smaller than a predetermined number. In one implementation, the predetermined number is two. In such an implementation, the row number and the column number of each pixel of the second pixels subset should satisfy the following conditions:

$$|r_{pn} - r_{p2}| < 2 \text{ and } |c_{pn} - c_{p2}| < 2$$

where $r_{pn}$ is the row number of a pixel in the second pixels subset, $r_{p2}$ is the row number of the second pixel 216, $c_{pn}$ is the column number of a pixel in the second pixels subset, and $c_{p2}$ is the column number of the second pixel 216.

In some implementations, the peak size threshold may be set by an operation defined by $$C_1 = w'^2 - \alpha' \quad (2)$$

where $C_1$ is the peak size threshold, w' is the width of the two-dimensional window 204, and $\alpha'$ is a constant. In an implementation, the constant $\alpha'$ should satisfy the following condition: $1 \leq \alpha' \leq w'^2$.

In some implementations, generating the peak-detected image (step 108) may include selecting a third pixel 222 from the plurality of pixels 202, where the third pixel 222 is not included in the plurality of true peaks, selecting a second true peak 224 from the plurality of true peaks, where the intensity level of the second true peak 224 is smaller than the intensity threshold, and setting the intensity levels of the third pixel 222 and the second true peak 224 to zero. The third pixel 222 is represented in bright gray and the second true peak 224 is represented in dark gray in FIG. 2, to illustrate that the second true peak 224 has a higher intensity level than the third pixel 222, but a lower intensity level than the first true peak 220 that is represented in black. Therefore, in some implementations, the peak-detected image may be described as a matrix P with the same size as matrix $I_F$, in which all elements may be zero except the elements with the same address as the address of true peaks that have a higher intensity level than the intensity threshold. The intensity levels of true peaks with higher intensity levels than the intensity threshold may be assigned to the corresponding elements of P.

In some implementations, the intensity threshold may be calculated by an operation defined by $$I_{min} = thr \times sum_{nz}/N_{nz} \quad (3)$$

where $I_{min}$ is the intensity threshold, thr is a constant between zero and one, $sum_{nz}$ is the sum of the intensity levels of the plurality of pixels 202, and $N_{nz}$ is the number of elements of a third pixels subset from the plurality of pixels 202. In some cases, the intensity level of each element in the third pixels subset is non-zero.

In order to obtain a more qualified and accurate peak-detected image, a post-processing operation may be conducted on the peak-detected image in some implementations. For this purpose, the method 100 may further include detecting an updated plurality of local peaks in the peak-detected image, detecting an updated plurality of true peaks among the updated plurality of local peaks, replacing the plurality of true peaks with the updated plurality of true peaks, generating an updated peak-detected image from the peak-detected image, and replacing the peak-detected image with the updated peak-detected image. The updated peak-detected image may include an updated true peaks subset from the plurality of true peaks.

In some implementations, detecting the updated plurality of local peaks may be performed in a similar manner as detecting the plurality of local peaks 208, except that the updated plurality of local peaks may be detected in the peak-detected image, rather than the smooth image 200. In addition, the width of the two-dimensional window 204 (w') may be changed for detecting the updated plurality of local peaks. In other implementations, detecting the updated plurality of true peaks may be performed in a similar manner as that of detecting the plurality of true peaks, except that the value of the peak size threshold may be changed according to a new value for the width of the two-dimensional window 204 (w'), and a new value for the constant α'. In one implementation, the new value of α' should still satisfy the condition $1 \leq \alpha' \leq w'^2$. In different implementations, generating the updated peak-detected image may be performed in a similar manner as that of generating the peak-detected image, except that the updated peak-detected image is generated from the peak-detected image, rather than the smooth image 200.

Figure 3:
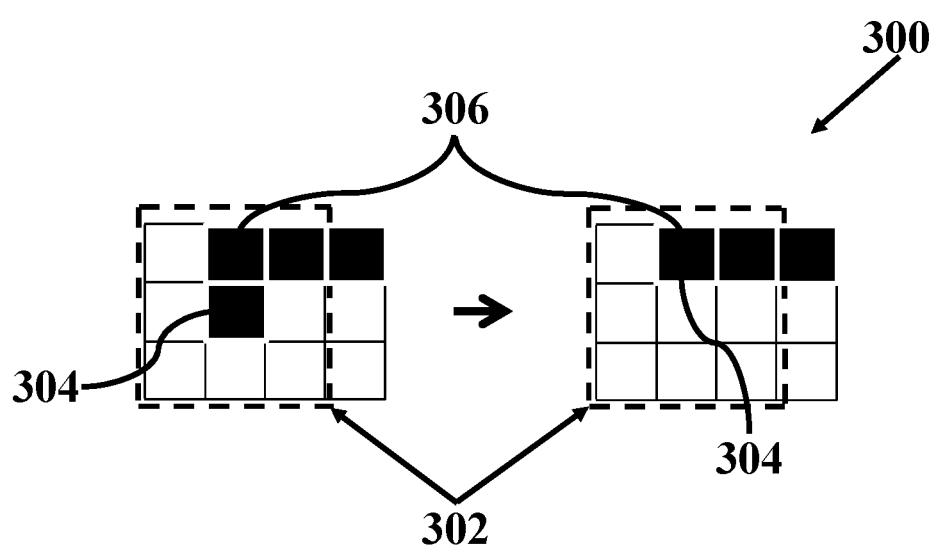
FIG. 3 illustrates an implementation of localizing true peaks in a peak-detected image.

FIG. 3 illustrates an implementation 300 of localizing true peaks in the peak-detected image. Localizing may be performed to decrease the effects of noise on the position of the true peaks. In some implementations, localizing at least one true peak of the first true peaks subset (step 104) may include defining a square region 302 around a third true peak 304 from the first true peaks subset, where the third true peak 304 may be located at the center of the square region 302, calculating a center of mass 306 of the square region 302, and relocating the third true peak 304 to the center of mass 306 of the square region.

Figure 4:
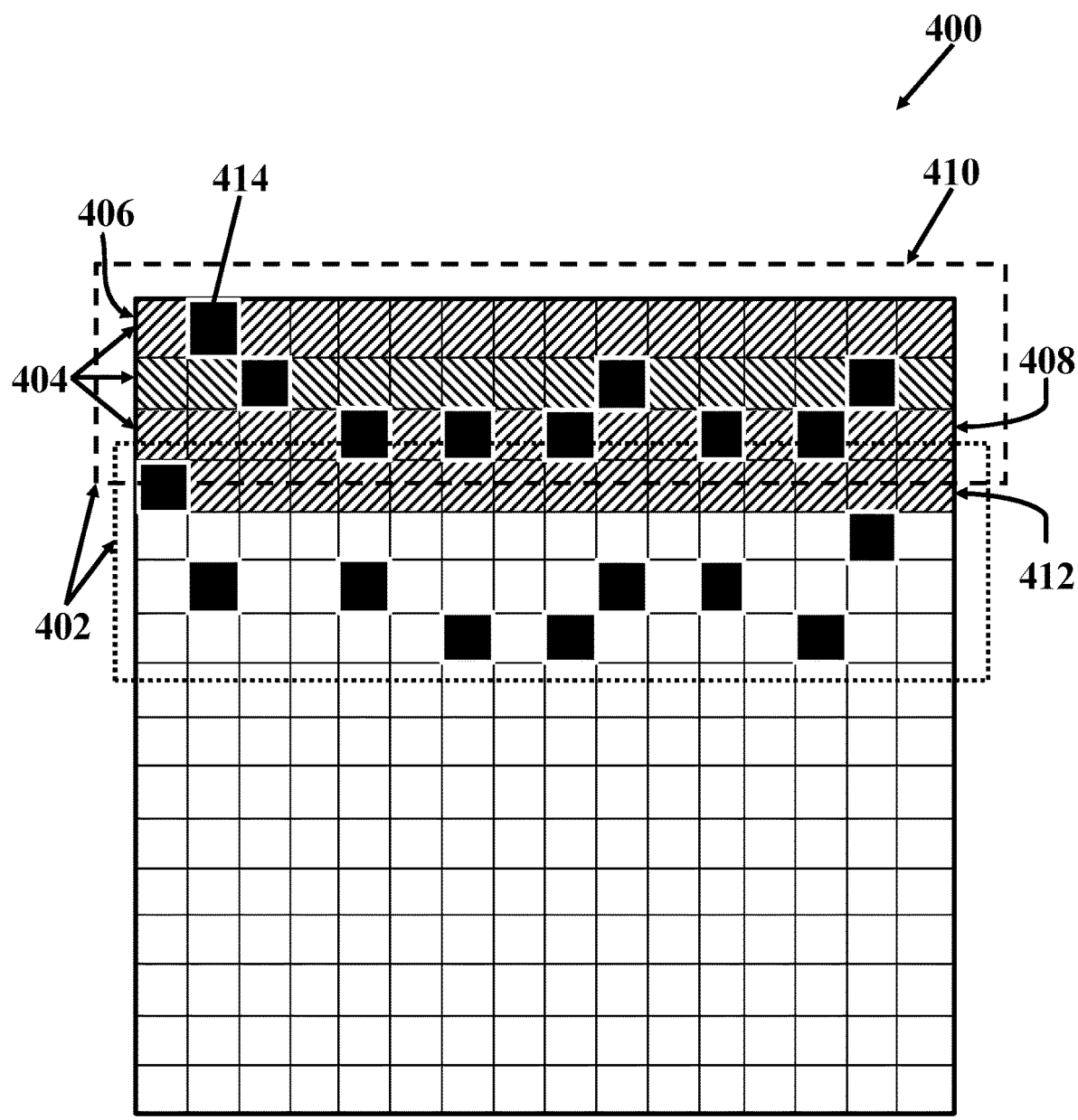
FIG. 4 illustrates an implementation of a peak-detected image including a plurality of bands.

FIG. 4 illustrates one implementation of pixels in the peak-detected image 400. In some implementations, the method 100 may further include defining a plurality of bands 402 in the peak-detected image 400. Each band of the plurality of bands 402 may include a plurality of rows 404 of the peak-detected image. In some examples, the plurality of rows 404 may include a second true peaks subset from the plurality of true peaks. The number of elements in the second true peaks subset may be equal to a given peak number, or larger than the given peak number.

Figure 5:
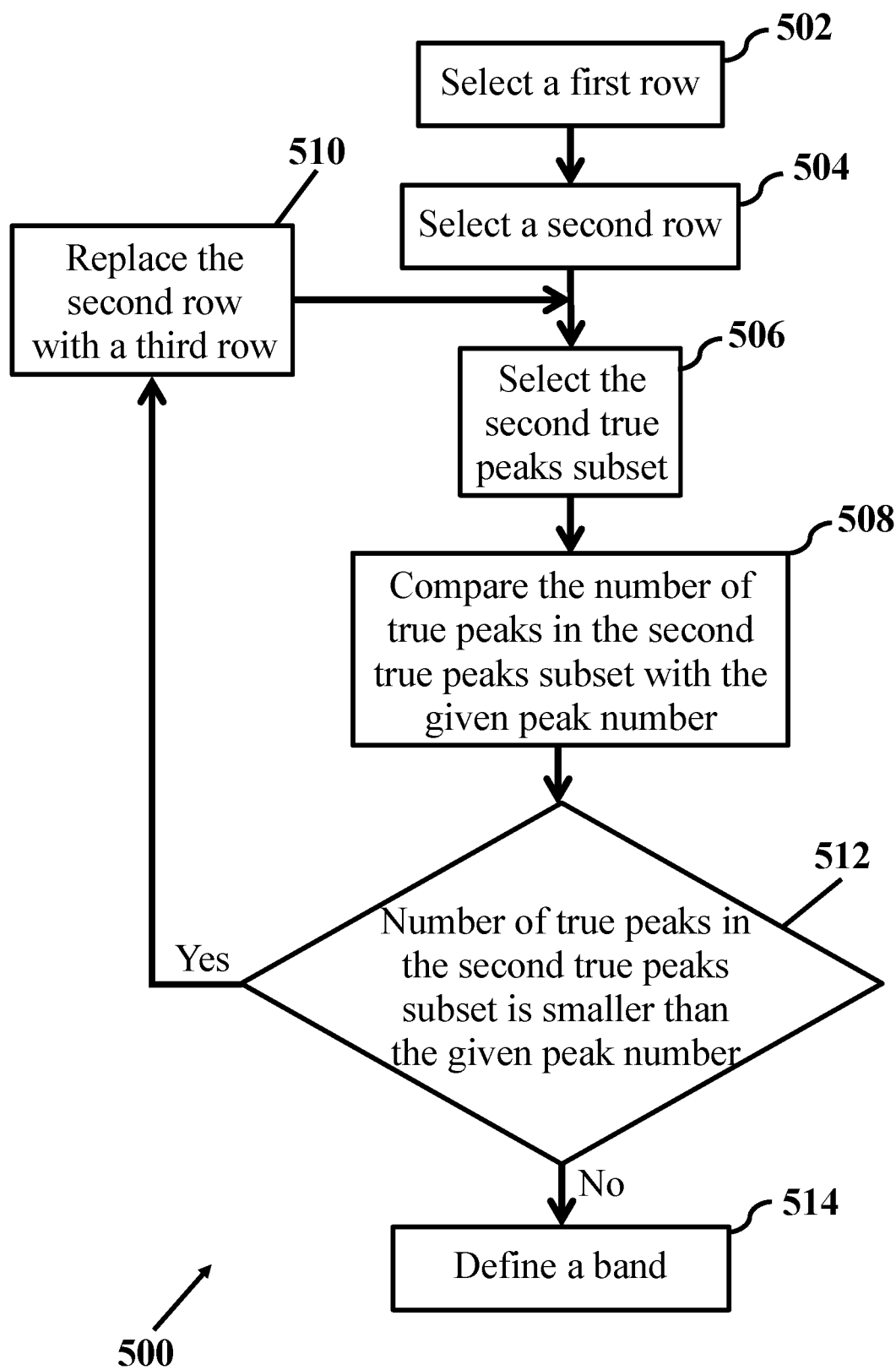
FIG. 5 is a flowchart illustrating an implementation of a process for defining a plurality of bands in a peak detected image.

FIG. 5 illustrates a flowchart of an implementation of a procedure 500 for defining the plurality of bands 402. In some implementations, defining the plurality of bands 402 may include selecting a first row 406 from the plurality of rows 404 (step 502), selecting a second row 408 from the plurality of rows 404 (step 504), and selecting the second true peaks subset from the plurality of true peaks (step 506), where each true peak 414 in the second true peaks subset may be located in the first row 406 or in the second row 408 or in a portion of the peak-detected image 400 between the first row 406 and the second row 408. Once the second true peaks subset is selected, the procedure 500 may compare the number of true peaks in the second true peaks subset with the given peak number (step 508), and replace the second row with a third row of the plurality of rows 404 (step 510), if the number of true peaks in the second true peaks subset is smaller than the given peak number (step 512, Yes). However, if the number of true peaks in the second true peaks subset is equal to or larger than the given peak number (step 512, No), the procedure 500 may define a band 410 of the plurality of bands 402 (step 514) as a rows subset in the peak-detected image. In some implementations, the rows subset may include the first row 406, the second row 408 and a portion of the peak-detected image 400 between the first row and the second row 408. In some examples, the third row may be located below the second row 408. Initially, the second row 408 may be equal to the first row 406. In some implementations, selecting the second true peaks subset, comparing the number of true peaks in the second true peaks subset with the given peak number, and replacing the second row 408 with the third row may be repeated in a cycle until the number of true peaks in the second true peaks subset becomes equal to or larger than the given peak number.

Referring again to FIG. 4, in some implementations defining the plurality of bands 402 may further include replacing the first row 406 with a fourth row 412 in the peak-detected image 400 after the band 410 in the plurality of bands 402 is defined, if the second row 408 is not a last row in the peak-detected image 400. In some examples, the fourth row 41 may be located below the second row 408.

EXAMPLE

Peak Detection in a Two-Dimensional Flood-Field Image

Figure 6:
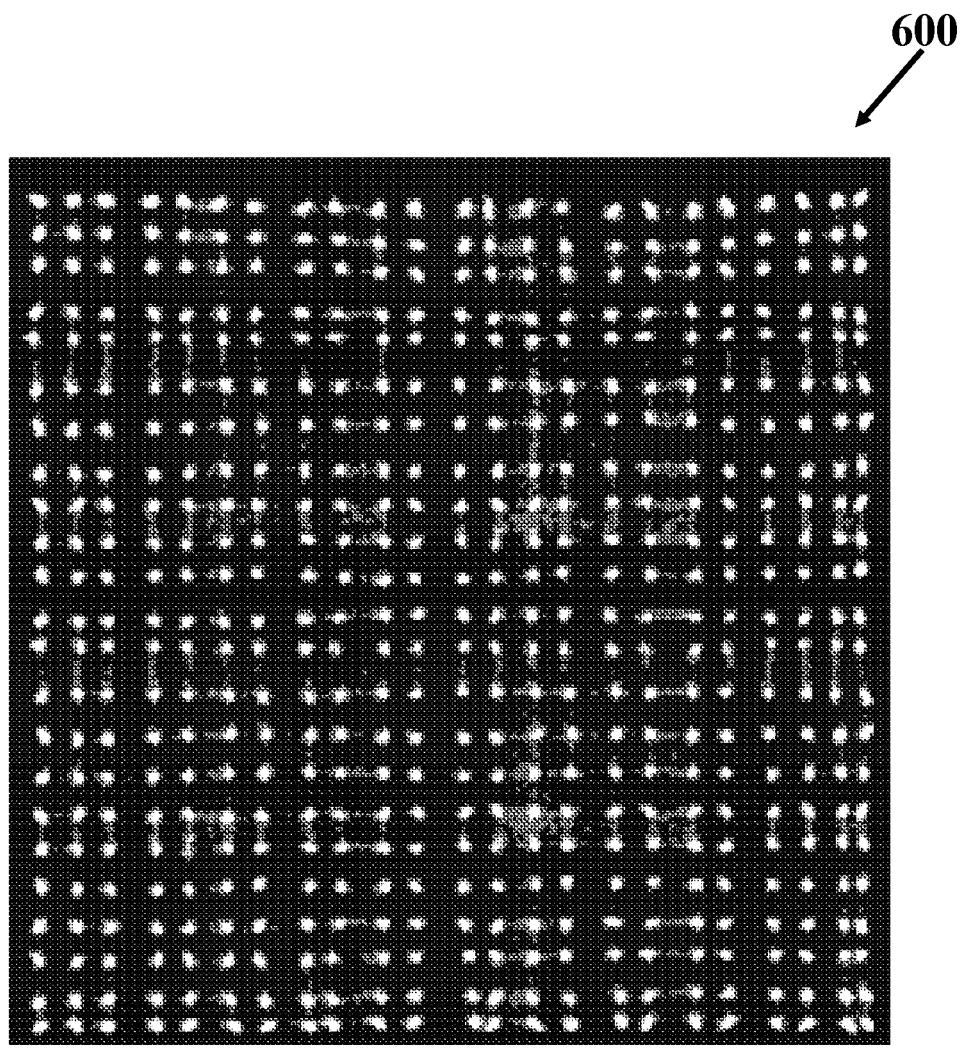
FIG. 6 illustrates an example flood-field image.

FIG. 6 illustrates an example flood-field image 600. The flood-field image 600 is generated by a detector including an array of 23×23 LYSO crystals (with a of 2×2 mm² pixel size) coupled with an array of 12×12 Silicon photomultiplier (SiPM) photodiodes. The size of the SiPM array is 50.2× 50.2 mm² (with a 4.2×4.2 mm² pixel pitch). Since the LYSO crystals have an intrinsic radioactivity, there may be no need to use external sources for generating the flood-field image 600.

Figure 7:
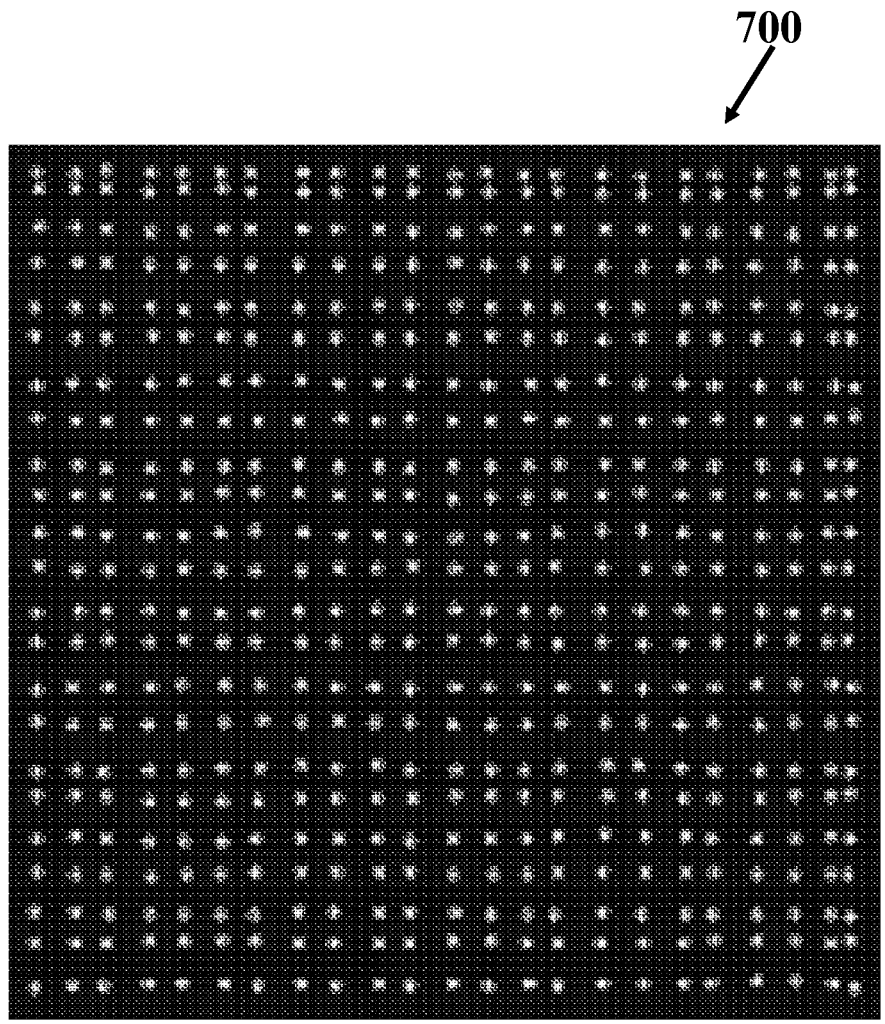
FIG. 7 illustrates an example peak-detected image generated by applying an implementation of a peak detection method on a flood-field image.

FIG. 7 illustrates an example peak-detected image 700, which is generated by applying an implementation of the method 100 on the flood-field image 600, to automatically determine the position of the true peaks in the flood-field image 600. As shown in FIG. 7, most of the background noise and distortions of size and position of the true peaks in the flood-field image 600 are removed in the peak-detected image 700, and each true peak is easily recognizable from other true peaks in the peak-detected image 700.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for peak detection in a two-dimensional image, the method comprising:
generating a smooth image from the two-dimensional image, the smooth image comprising a plurality of pixels, wherein each pixel of the plurality of pixels has an intensity level and an address, the address comprising a row number and a column number;
detecting a local peak of the plurality of local peaks in the smooth image, detecting the local peak comprising:
placing a two-dimensional window on a portion of the smooth image;
selecting a first pixels subset from the plurality of pixels, the first pixels subset located inside the two-dimensional window; and
detecting the local peak by selecting a first pixel in the first pixels subset as the local peak, the first pixel comprising a highest intensity level in the first pixels subset;
detecting a true peak of the plurality of true peaks among the plurality of local peaks;
generating a peak-detected image from the smooth image, the peak-detected image comprising a first true peaks subset from the plurality of true peaks, wherein the intensity level of each true peak of the plurality of true peaks in the first true peaks subset is higher than, an intensity threshold; and
localizing at least one true peak in the first true peaks subset in the peak-detected image.

2. The method of claim 1, wherein generating the smooth image includes applying a smoothing function on the two-dimensional image.

3. The method of claim 2, wherein the smoothing function includes a normalized two-dimensional Gaussian filter.

4. The method of claim 1, further comprising:
detecting an updated plurality of local peaks in the peak-detected image;
detecting an updated plurality of true peaks among the updated plurality of local peaks;
replacing the plurality of true peaks with the updated plurality of true peaks;

generating an updated peak-detected image from the peak-detected image, wherein the updated peak-detected image includes an updated true peaks subset from the plurality of true peaks; and
replacing the peak-detected image with the updated peak-detected image.

5. The method of claim 1, wherein localizing at least one true peak of the first true peaks subset comprises:
defining a square region around a third true peak from the first true peaks subset, wherein the third true peak is located at the center of the square region;
calculating a center of mass of the square region; and
relocating the third true peak to the center of mass of the square region.

6. The method of claim 1, wherein detecting the true peak comprises:
defining a neighborhood around a second pixel of the plurality of pixels;
selecting a local peaks subset from the plurality of local peaks, wherein the local peaks subset is located in the neighborhood; and
selecting the second pixel as a first true peak of the plurality of true peaks, if a size of the local peaks subset is larger than a peak size threshold.

7. The method of claim 6, wherein the neighborhood includes a second pixels subset from the plurality of pixels, wherein an absolute difference of the row number of each pixel of the second pixels subset and the row number of the second pixel is smaller than a predetermined number, and an absolute difference of the column number of each pixel of the second pixels subset and the column number of the second pixel is smaller than the predetermined number.

8. The method of claim 6, wherein the peak size threshold is set by an operation defined by $$C_1 = w'^2 - \alpha'; \text{ and}$$

$$1 \leq \alpha' \leq w'^2,$$

where $C_1$ is the peak size threshold, $w'$ is the width of the two-dimensional window, and $\alpha'$ is a constant.

9. The method of claim 6, wherein generating the peak-detected image comprises:
selecting a third pixel from the plurality of pixels, wherein the third pixel is not included in the plurality of true peaks;
selecting a second true peak from the plurality of true peaks, wherein the intensity level of the second true peak is smaller than the intensity threshold; and
setting the intensity levels of the third pixel and the second true peak to zero.

10. The method of claim 9, wherein the intensity threshold is calculated b an operation defined by $$I_{min} = thr \times sum_{nz}/N_{nz}$$

where $I_{min}$ is the intensity threshold, thr is a constant between zero and one, $sum_{nz}$ is the sum of the intensity levels of the plurality of pixels, and $N_{nz}$ is the number of elements of a third pixels subset from the plurality of pixels, wherein the intensity level of each element in the third pixels subset is non-zero.

11. A method for peak detection in a two-dimensional image, the method comprising:
generating a smooth image from the two-dimensional image, the smooth image comprising a plurality of pixels, wherein each pixel of the plurality of pixels has an intensity level and an address, the address comprising a row number and a column number;
detecting a local peak of the plurality of local peaks in the smooth image;
detecting a true peak of the plurality of true peaks among the plurality of local peaks;
generating a peak-detected image from the smooth image, the peak-detected image comprising a first true peaks subset from the plurality of true peaks, wherein the intensity level of each true peak of the plurality of true peaks in the first true peaks subset is higher than an intensity threshold;
localizing at least one true peak in the first true peaks subset in the peak-detected image; and
defining a plurality of bands in the peak-detected image, each band of the plurality of bands including, a plurality of rows of the peak-detected image, the plurality of rows including a second true peaks subset from the plurality of true peaks, wherein a number of true peaks in the second true peaks subset is equal to or larger than a given peak number.

12. The method of claim 11, wherein defining the plurality of bands comprises:
selecting a first row from the plurality of rows;
selecting a second row from the plurality of rows, wherein the second row is equal to the first row;
selecting the second true peaks subset from the plurality of true peaks, wherein each true peak in the second true peaks subset is located in the first row, or in the second row, or in a portion of the peak-detected image between the first row and the second row;
comparing the number of true peaks in the second true peaks subset with the given peak number;
replacing the second row with a third row of the plurality of rows if the number of true peaks in the second true peaks subset is smaller than the given peak number, wherein the third row is located below the second row, wherein selecting the second true peaks subset, comparing the number of true peaks in the second true peaks subset with the given peak number, and replacing the second row with the third row are repeated in a cycle until the number of true peaks in the second true peaks subset, becomes equal to or larger than the given peak number; and
defining a band of the plurality of bands as a rows subset in the peak-detected image, if the number of true peaks in the second true peaks subset is equal to or larger than the given peak number, wherein the rows subset includes the first row, the second row, and a portion of the peak detected image between the first row and the second row.

13. The method of claim 12, wherein defining the plurality, of bands further comprises replacing the first row with a fourth row in the peak-detected image after the band in the plurality of bands is defined, if the second row is not a last row in the peak-detected image, wherein the fourth row is located below the second row.

14. A method for peak detection in a two-dimensional image, the method comprising: generating a smooth image from the two-dimensional image, the smooth image comprising a plurality of pixels has an intensity level and an address, the address comprising a row number and a column number,
detecting a true peak of the plurality of true peaks among the plurality of local peaks;
generating a peak-detected image from the smooth image, the peak-detected image comprising a first true peaks subset from the plurality of true peaks, wherein the intensity level of each true peak of the plurality of true peaks in the first true peaks subset is higher than an intensity threshold; and localizing, at least one true peak in the first true peaks subset in the peak-detected image.

15. The method of claim 14, wherein generating the smooth, image includes generating the smooth image from the digitized food-field image generated in the gamma detector of a positron emission tomography (PET) imaging system, or a single-photon emission computed tomography (SPECT) imaging system.

16. The method of claim 14, wherein generating the smooth image includes generating the smooth image from the digitized flood-field image generated in a plurality of pixelated scintillation crystals optically coupled with an array of photodetectors.

17. The method of claim 15, wherein the digitized flood-field image is used in a calibration process including a positioning calibration in the positron emission tomography (PET) imaging system, or a linearity calibration in the single-photon emission computed tomography (SPECT) imaging, system.

18. The method of claim 17, wherein the positioning calibration and the linearity calibration include irradiating the plurality of pixelated scintillation crystals by a uniform radiation source.

19. The method of claim 17, wherein the positioning, calibration and the linearity calibration include radiation from the plurality of pixelated scintillation crystals, the plurality of pixelated scintillation crystals including a plurality of Lutetium based crystals.

* * * * *